United States Patent
Takahashi et al.

(10) Patent No.: US 9,662,037 B2
(45) Date of Patent: May 30, 2017

(54) MAGNETIC RESONANCE IMAGING APPARATUS AND MAGNETIC RESONANCE IMAGING METHOD

(75) Inventors: Naho Takahashi, Otawara (JP); Masao Yui, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1517 days.

(21) Appl. No.: 13/354,775

(22) Filed: Jan. 20, 2012

(65) Prior Publication Data

US 2012/0119740 A1 May 17, 2012

Related U.S. Application Data

(63) Continuation of application No. PCT/JP2011/073018, filed on Oct. 5, 2011.

(30) Foreign Application Priority Data

Oct. 19, 2010 (JP) ................................ 2010-235010

(51) Int. Cl.
  *G01V 3/00* (2006.01)
  *A61B 5/055* (2006.01)
  (Continued)

(52) U.S. Cl.
  CPC ............ *A61B 5/055* (2013.01); *A61B 5/0037* (2013.01); *G01R 33/48* (2013.01)

(58) Field of Classification Search
  CPC ...................................................... G01R 33/48
  (Continued)

(56) References Cited

U.S. PATENT DOCUMENTS 6,091,242 A * 7/2000 Hanawa ............. G01R 33/4833
  324/300
2007/0229070 A1* 10/2007 Miyazaki ............... G01N 24/08
  324/307

(Continued)

FOREIGN PATENT DOCUMENTS

JP  4-51935   2/1992
JP  7-95971   4/1995
(Continued)

OTHER PUBLICATIONS

Office Action issued Jan. 24, 2014, in CN Patent Application No. 201180002345.5.
(Continued)

*Primary Examiner* — Louis Arana
(74) *Attorney, Agent, or Firm* — Nixon & Vanderhye P.C.

(57) ABSTRACT

According to one embodiment, a magnetic resonance imaging apparatus includes a spectrum acquisition unit, a resonance frequency acquisition unit and an imaging unit. The spectrum acquisition unit is configured to acquire frequency spectra of magnetic resonance signals from an object while changing a suppression effect or an enhancing effect of signals from a specific material. The resonance frequency acquisition unit is configured to obtain a resonance frequency of the specific material or another material based on an index representing a difference in intensities of signals from the specific material or the another material between the frequency spectra. The imaging unit is configured to perform imaging using a radio frequency pulse having a center frequency set to the resonance frequency of the specific material or the another material.

9 Claims, 7 Drawing Sheets

(51) Int. Cl.
*G01R 33/48* (2006.01)
*A61B 5/00* (2006.01)

(58) Field of Classification Search
USPC .............................. 324/307, 309, 314, 300
See application file for complete search history.

(56) References Cited

U.S. PATENT DOCUMENTS

| | | | | |
|---|---|---|---|---|
| 2008/0238421 | A1* | 10/2008 | Kitane | G01R 33/4828 324/307 |
| 2009/0137897 | A1* | 5/2009 | Balchandani | A61B 5/05 600/410 |
| 2013/0249552 | A1* | 9/2013 | Imamura | G01R 33/4828 324/309 |

FOREIGN PATENT DOCUMENTS

| | | |
|---|---|---|
| JP | 7-327954 | 12/1995 |
| JP | 11-76193 | 3/1999 |
| JP | 2009-34152 | 2/2009 |

OTHER PUBLICATIONS

Office Action issued Apr. 21, 2015 in JP Patent Application No. 2011-221303.
Notification of Transmittal of Translation of the International Preliminary Report on Patentability in PCT/JP2011/073018 mailed May 16, 2013.
International Search Report for PCT/JP2011/073018, mailed Dec. 27, 2011.

* cited by examiner

MAGNETIC RESONANCE IMAGING APPARATUS AND MAGNETIC RESONANCE IMAGING METHOD

CROSS REFERENCE

This is a continuation of Application PCT/JP2011/073018, filed Oct. 5, 2011.

This application is based upon and claims the benefit of priority from Japanese Patent Application No. 2010-235010, filed Oct. 19, 2010; the entire contents of which are incorporated herein by reference.

FIELD

Embodiments described herein relate generally to a MRI (magnetic resonance imaging) apparatus and a magnetic resonance imaging method.

BACKGROUND

MRI is an imaging method which excites nuclear spin of an object set in a static magnetic field with a RF (radio frequency) signal having the Larmor frequency magnetically and reconstructs an image based on MR (magnetic resonance) signals generated due to the excitation.

In MRI, a center frequency of a RF pulse is set to the resonance frequency of water which is a target of signal acquisition. Therefore, a pre-scan is performed for acquiring a frequency spectrum of signals prior to an imaging scan in order to detect peaks of resonance frequencies mutually different between materials. The resonance frequency of water shifts from that of fat relatively by about 3.5 ppm (parts per million). Therefore, a fat saturation pulse is applied in a pre-scan ordinarily so that a peak does not appear at the frequency corresponding to fat in a frequency spectrum. The fat saturation pulse is a RF pulse for suppressing signals from fat.

Then, a peak is detected from the frequency spectrum having been acquired by the pre-scan, and subsequently, a frequency corresponding to the detected peak is set to the center frequency of RF pulses as the resonance frequency of water.

However, if fat component abounds in an imaging region like a case of imaging a chest part especially, fat suppression becomes insufficient. Consequently, a shape of a frequency spectrum is disturbed and it becomes difficult to detect a frequency corresponding to a water peak with a high degree of accuracy. Sometimes a peak larger than that corresponding to water appears at the resonance frequency of fat. Hence, there is the possibility of recognizing the resonance frequency of fat as that of water erroneously.

On the other hand, detection of the resonance frequency of water and set up of the center frequency of RF pulses are desired to be automated. Therefore, it is important to detect the resonance frequency of water with a sufficient accuracy without fail not only in a case of detecting the resonance frequency of water by visual check of a frequency spectrum by a user to match the center frequency of RF pulses with the resonance frequency of water but also in a case of automatically detecting the resonance frequency of water and setting the center frequency of RF pulses.

The same concerns apply to a case of setting the center frequency of RF pulses to a resonance frequency of a material other than water for molecular imaging which generates MR signals from a specific material for imaging.

An object of the present invention is to provide a magnetic resonance imaging apparatus and a magnetic resonance imaging method which can detect a resonance frequency of a material, such as water, which is a target of signal acquisition with higher accuracy.

PRIOR TECHNICAL LITERATURE

[Patent literature 1] JPA 2005-270327

DETAILED DESCRIPTION

In general, a magnetic resonance imaging apparatus of an embodiment according to the present invention includes a spectrum acquisition unit, a resonance frequency acquisition unit and an imaging unit. The spectrum acquisition unit acquires frequency spectra of magnetic resonance signals from an object while changing a suppression effect or an enhancing effect of signals from a specific material. The resonance frequency acquisition unit obtains a resonance frequency of the specific material or another material based on an index representing a difference in intensities of signals from the specific material or the another material between the frequency spectra. The imaging unit performs imaging using a radio frequency pulse of which the center frequency is set to the resonance frequency of the specific material or the another material.

Further, a magnetic resonance imaging apparatus of an embodiment according to the present invention includes a spectrum acquisition unit, a resonance frequency acquisition unit and an imaging unit. The spectrum acquisition unit is configured to acquire a frequency spectrum of magnetic resonance signals from an object while suppressing or enhancing signals from a specific material. The resonance frequency acquisition unit is configured to obtain a resonance frequency of the specific material or another material based on an index representing an equality degree or an inequality degree between the frequency spectrum and a frequency spectrum for reference. The imaging unit is configured to perform imaging using a radio frequency pulse of which the center frequency is set to the resonance frequency of the specific material or another material.

Further, a magnetic resonance imaging method of an embodiment according to the present invention includes acquiring frequency spectra of magnetic resonance signals from an object while changing a suppression effect or an enhancing effect of signals from a specific material; obtaining a resonance frequency of the specific material or another material based on an index representing a difference in intensities of signals from the specific material or the another material between the frequency spectra; and performing imaging using a radio frequency pulse of which the center frequency is set to the resonance frequency of the specific material or the another material.

A magnetic resonance imaging apparatus and a magnetic resonance imaging method according to embodiments of the present invention will be described with reference to the accompanying drawings.

First Embodiment

Figure 1:
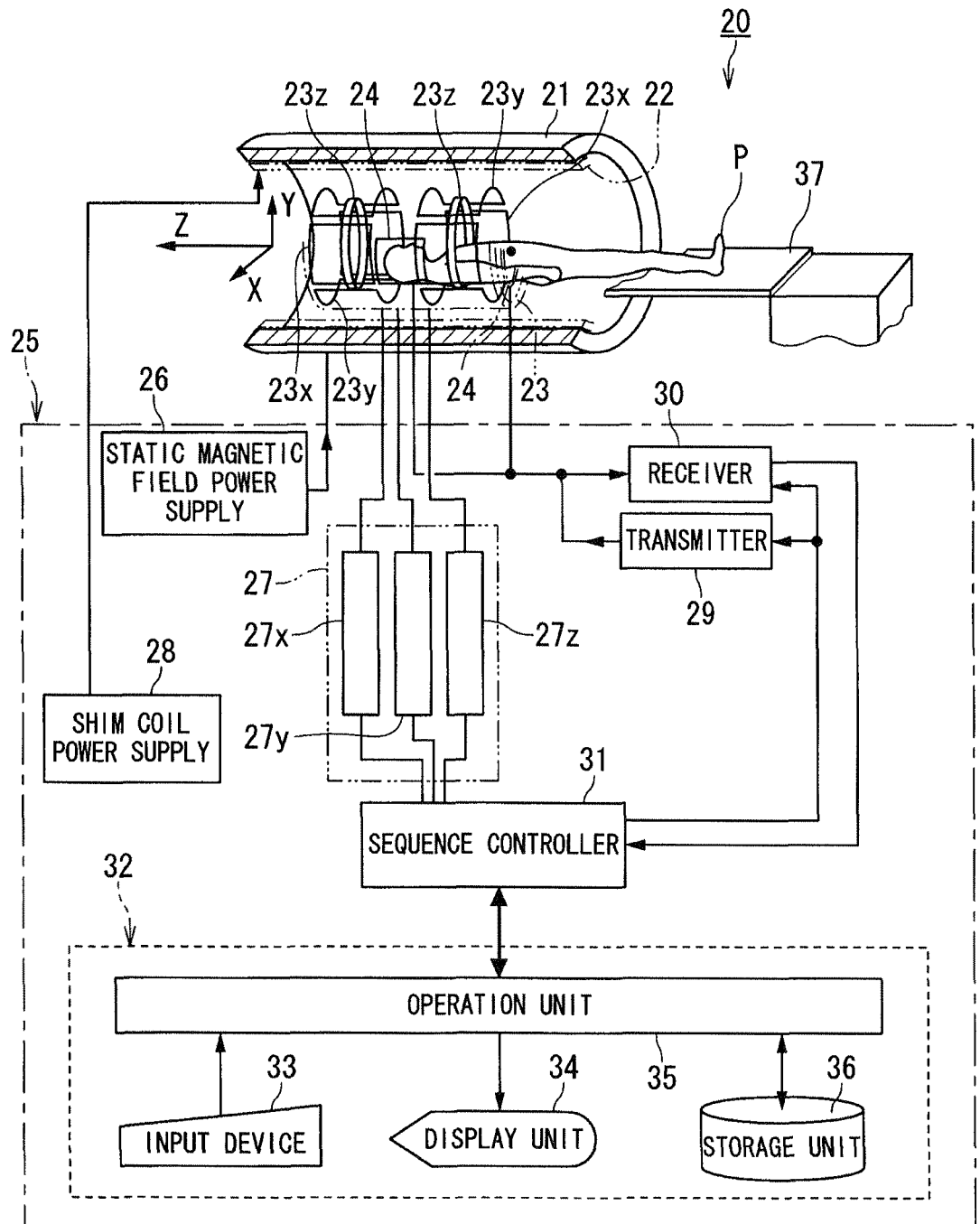
FIG. 1 is a block diagram showing a magnetic resonance imaging apparatus according to the first embodiment of the present invention.

FIG. 1 is a block diagram showing a magnetic resonance imaging apparatus according to the first embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The RF coils 24 communicate with at least one of the transmitter 29 and the receiver 30. The transmission RF coil 24 has a function to transmit a RF signal given from the transmitter 29 to the object P. The reception RF coil 24 has a function to receive a MR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex data obtained through the detection of a MR signal and A/D (analog to digital) conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

Figure 2:
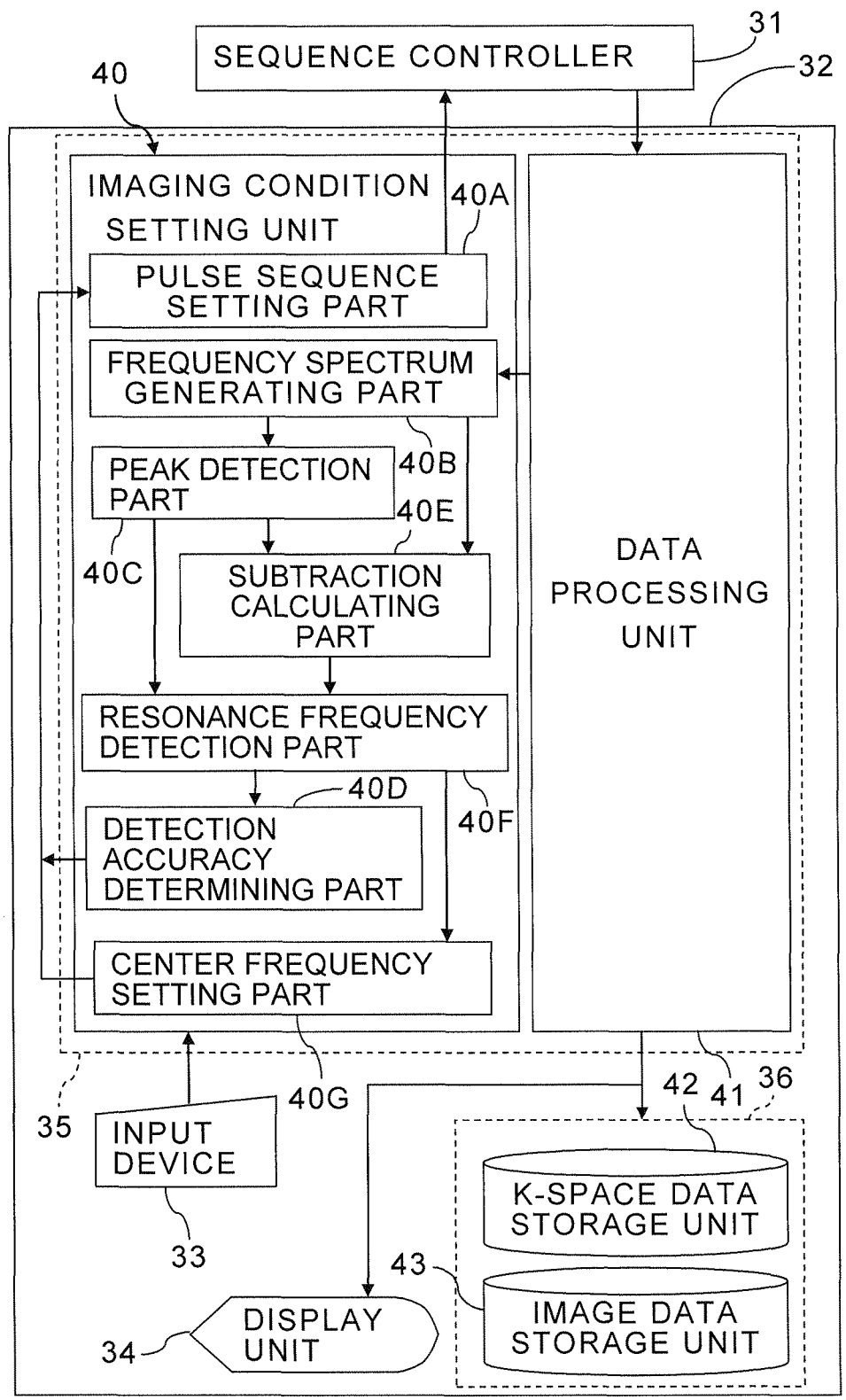
FIG. 2 is a functional block diagram of the computer shown in FIG. 1.

FIG. 2 is a functional block diagram of the computer 32 shown in FIG. 1.

The operation unit 35 of the computer 32 functions as an imaging condition setting unit 40 and a data processing unit 41 by executing program stored in the storage unit 36. Meanwhile, the storage unit 36 functions as a k-space data storage unit 42 and an image data storage unit 43. The imaging condition setting unit 40 has a pulse sequence setting part 40A, a frequency spectrum generating part 40B, a peak detection part 40C, a detection accuracy determining part 40D, a subtraction calculating part 40E, a resonance frequency detection part 40F and a center frequency setting part 40G.

The imaging condition setting unit 40 has a function to set imaging conditions including a pulse sequence and output the set imaging conditions to the sequence controller 31 to control the sequence controller 31. Especially, the imaging condition setting unit 40 has a function to set imaging conditions for a pre-scan for acquiring a frequency spectrum of MR signals in addition to imaging conditions for imaging. A frequency spectrum is generally acquired by a pre-scan for shimming which determines currents to be supplied to the shim coil 22 from the shim coil power supply 28. Then, the acquired frequency spectrum is used for setting the center frequency of RF pulses which is one of imaging conditions for imaging.

In addition, the imaging condition setting unit 40 has a function to obtain a resonance frequency of a specific material or another material based on an index representing a difference in intensity of MR signal from the specific material or the other material between mutually different frequency spectra acquired with changing suppression effect or enhancing effect of signals from the specific material such as water or fat.

The pulse sequence setting part 40A has a function to set a pulse sequence for a pre-scan to acquire mutually different frequency spectra of MR signals from an object P with changing suppression effect or enhancing effect of signals from the specific material as well as a pulse sequence for an imaging scan. Hereinafter, a case of acquiring two frequency spectra will be described.

Figure 3:
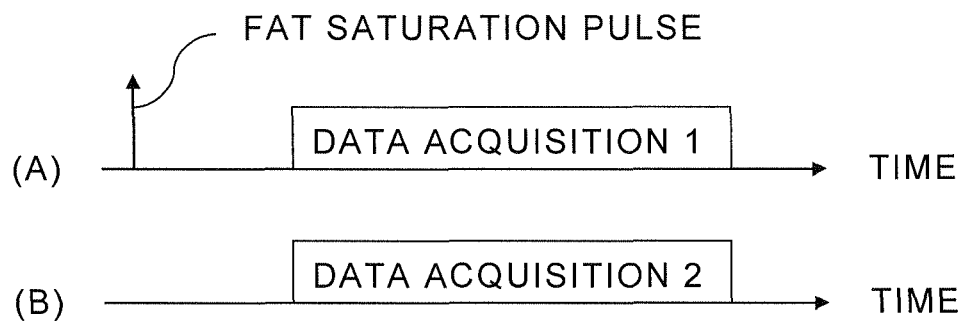
FIG. 3 is a chart showing the first example of sequences set by the pulse sequence setting part shown in FIG. 2.

FIG. 3 is a chart showing the first example of sequences set by the pulse sequence setting part 40A shown in FIG. 2.

In FIG. 3, the abscissa axis denotes time. Performing a pre-scan two times with the first sequence for acquiring data after applying a fat saturation pulse as shown in FIG. 3 (A) and the second sequence for acquiring data without applying a fat saturation pulse as shown in FIG. 3 (B) can acquire two sets of MR data showing mutually different fat saturation effects. Therefore, when the first frequency spectrum is generated from the first MR data acquired by the first sequence and the second frequency spectrum is generated from the second MR data acquired by the second sequence, the suppression effect of fat signals in the first frequency spectrum becomes different from that in the second frequency spectrum.

Figure 4:
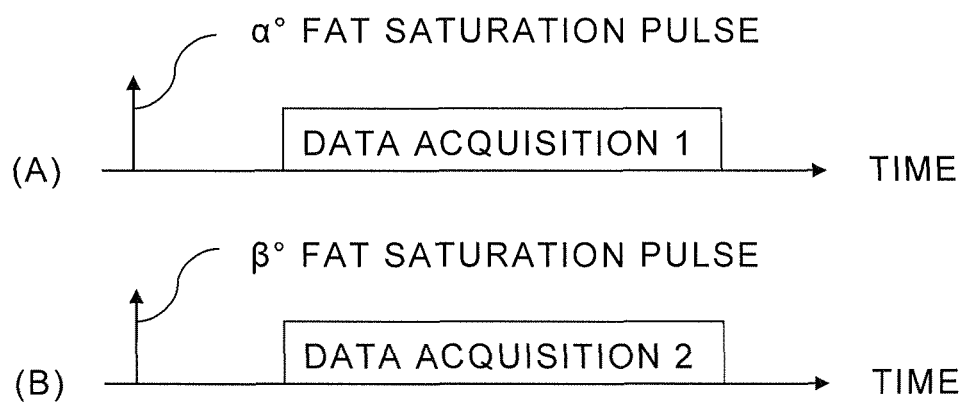
FIG. 4 is a chart showing the second example of sequences set by the pulse sequence setting part shown in FIG. 2.

FIG. 4 is a chart showing the second example of sequences set by the pulse sequence setting part 40A shown in FIG. 2.

In FIG. 4, the abscissa axis denotes time. Performing a pre-scan two times with the first sequence for acquiring data after applying a fat saturation pulse of which FA (flip angle) is $\alpha°$ as shown in FIG. 4 (A) and the second sequence for acquiring data after applying a fat saturation pulse of which FA is $\beta°$ different from $\alpha°$ as shown in FIG. 4 (B) can also acquire two sets of MR data showing mutually different fat saturation effects. Therefore, two frequency spectra showing mutually different fat suppression effects can be acquired.

Note that, the case where $\beta°$ shown in FIG. 4 (B) is set to be zero corresponds to the case of FIG. 3. That is, by changing a FA of a fat saturation pulse or whether a fat saturation pulse is applied, two frequency spectra showing mutually different fat suppression effects can be acquired.

Figure 5:
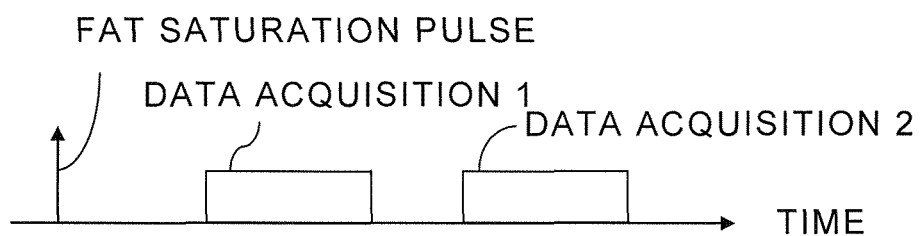
FIG. 5 is a chart showing the third example of sequence set by the pulse sequence setting part shown in FIG. 2.

FIG. 5 is a chart showing the third example of sequence set by the pulse sequence setting part 40A shown in FIG. 2.

In FIG. 5, the abscissa axis denotes time. A multi-echo data acquisition sequence for continuously acquiring the first MR data and the second MR data after applying a fat saturation pulse as shown in FIG. 5 can also acquire two frequency spectra showing mutually different fat suppression effects. Specifically, performing a pre-scan with the sequence shown in FIG. 5 can acquire the first MR data and the second MR data after mutually different elapsed times from an application time of the fat saturation pulse. Therefore, the first MR data shows a fat suppression effect different from that of the second MR data. Accordingly, when the first and second frequency spectra are generated from the first and second MR data respectively, the first and second frequency spectra show mutually different fat suppression effects.

That is to say, acquiring MR data two times while changing at least one parameter in imaging conditions influencing suppression or enhancing of signals from a specific material such as fat makes it possible to acquire two frequency spectra showing mutually different signal suppression effects or signal enhancing effects. Therefore, not only conditions with regard to a fat saturation pulse applied as a pre-pulse like the above-mentioned example but conditions with regard to a suppression pulse for suppressing or an excitation pulse for enhancing signals from another material may be changed. Alternatively, conditions in an imaging method for suppressing or enhancing a specific material selectively without applying a suppression pulse or an excitation pulse may be changed.

As a fat saturation pulse, a STIR (short TI inversion recovery) pulse, a CHESS (chemical shift selective) pulse, a SPIR (spectral presaturation with inversion recovery) pulse, a SPAIR (Spectral Attenuated Inversion Recovery) and the like are known. Further, a fat suppression method applying same or different fat saturation pulses is also known. Furthermore, a PASTA (polarity altered spectral-selective acquisition) sequence is known as a sequence for enhancing signals from water without applying pre-pulses. In addition, an imaging method for suppressing signals from silicone or water is also known.

In many cases, the center frequency of RF pulses in an imaging scan is adjusted to the resonance frequency of water. In this case, a frequency spectrum is acquired to detect the resonance frequency of water. Therefore, the explanation is made for a case of detecting the resonance frequency of water from a frequency spectrum in order to set the center frequency of RF pulses to the resonance frequency of water hereinafter.

It is the resonance frequency of fat distant from that of water by 3.5 ppm relatively in the negative direction that has high possibility to be recognized as the resonance frequency of water in error. Accordingly, a fat saturation pulse is conventionally applied so as to suppress a peak corresponding to fat signals in a frequency spectrum in a pre-scan for acquiring the frequency spectrum.

Note that, if silicone is included in a data acquisition region, a peak corresponding to signals from the silicone appears in a frequency spectrum at a frequency shifted in the negative direction from the resonance frequency of water by about 5 ppm. In this case, a silicone saturation pulse may be applied.

The pulse sequence setting part 40A sets imaging conditions for a pre-scan so that two frequency spectra to be acquired have mutually equivalent and distinct peaks corresponding to water signals and mutually different distribution shapes corresponding to fat signals as possible. For that purpose, it is preferable to set the first sequence after applying a STIR pulse, which influences nonuniformity of a static magnetic field little, as a fat saturation pulse and the second sequence without applying STIR pulses as the imaging conditions for a pre-scan.

A STIR sequence applying a STIR pulse is a sequence, under the SE (spin echo) sequence, for acquiring MR data by applying a 180° RF pulse as a STIR pulse to invert longitudinal magnetizations in a data acquisition part once and subsequently applying a 90° RF excitation pulse at a timing at which the longitudinal magnetization of fat recovers to become zero due to TI (longitudinal) relaxation. That is, the TI relaxation time of water is longer than that of fat. Therefore, acquiring data by applying an excitation pulse at a timing at which the longitudinal magnetization of fat becomes zero makes it possible to acquire water signals selectively.

Similarly, MR signals from a specific material can be suppressed or enhanced based on differences in TI relaxation time between the specific material and other materials because TI relaxation time varies depending on respective materials. Therefore, changing at least one condition such as a FA of a STIR pulse or whether a STIR pulse is applied makes it possible to acquire frequency spectra showing mutually different degrees of suppression or enhancing effect for signals from a specific material based on differences in TI relaxation time between the specific material and other materials.

The frequency spectrum generating part 40B has a function to generate a frequency spectrum based on MR data acquired by a pre-scan. Therefore, when the first and second pieces of MR data were acquired for generating two frequency spectra, the first and second frequency spectra are generated. MR data acquired by a pre-scan is supplied to the frequency spectrum generating part 40B from the data processing unit 41.

The peak detection part 40C has a function to detect a peak of a frequency spectrum generated in the frequency spectrum generating part 40B and a frequency corresponding to the peak. In addition, the peak detection part 40C is configured to calculate a distance between peaks and the maximum value when plural peaks were detected. Note that, the peak detection part 40C may be configured to determine whether another peak were detected at a frequency shifted from a frequency corresponding to the firstly detected peak by 3.5 ppm in the positive or negative direction.

The detection accuracy determining part 40D has a function to determine detection accuracy of peaks detected from a frequency spectrum acquired with fat suppression and control the imaging condition setting unit 40 so as not to perform a pre-scan for acquiring a frequency spectrum without fat suppression in case where the detection accuracy was determined to be a predetermined accuracy and sufficient. For example, the detection accuracy determining part 40D may be configured to control the pulse sequence setting part 40A so as not to generate a sequence for a pre-scan for acquiring a frequency spectrum without fat suppression.

Specifically, when a frequency spectrum acquired with fat suppression shows a clear peak at the resonance frequency of water so that the resonance frequency of water could be detected with sufficient accuracy, the center frequency of RF pulses can be set without acquiring another frequency spectrum. Accordingly, the imaging condition setting unit 40 is controlled by the detection accuracy determining part 40D so that an unnecessary pre-scan is not performed. Especially, when data was acquired from a part having a little fat, the resonance frequency of water is detected with sufficient accuracy in many cases.

Therefore, the detection accuracy determining part 40D preferably determines whether the resonance frequency of water was obtained with a predetermined accuracy, using a frequency spectrum showing a larger fat suppression effect. Then, acquisition of a frequency spectrum can be controlled so that a frequency spectrum showing smaller fat suppression effect is not acquired when the resonance frequency of water was determined to be obtained with the predetermined accuracy.

The subtraction calculating part 40E has a function to calculate an index representing each difference between distribution shapes corresponding to one or both of fat signals and water signals of two frequency spectra generated by the frequency spectrum generating part 40B. For example, a difference or a ratio of peak values corresponding to fat signals or water signals between two frequency spectra, or a difference or a ratio of integral values of signals in a certain frequency range between two frequency spectra can be used as an index mentioned above.

Figure 6:
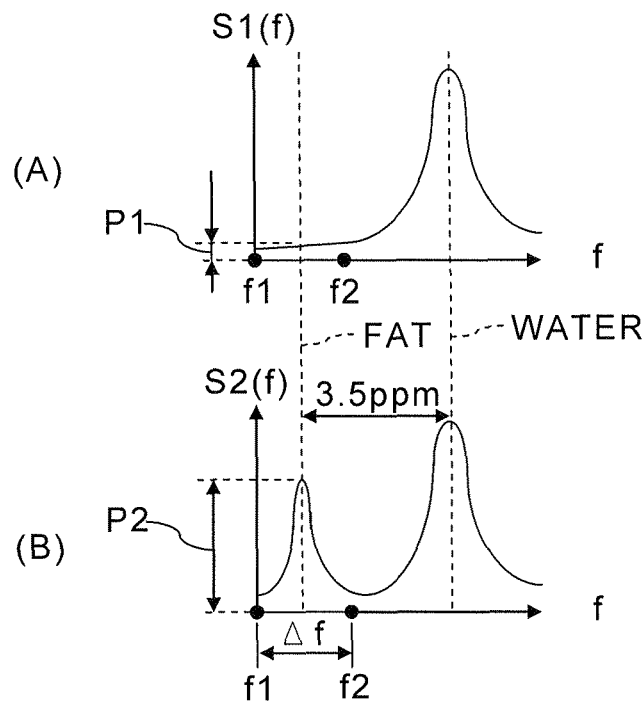
FIG. 6 shows the first example of two frequency spectra generated by the frequency spectrum generating part shown in FIG. 2.

FIG. 6 shows the first example of two frequency spectra generated by the frequency spectrum generating part 40B shown in FIG. 2.

In (A) and (B) of FIG. 6, each abscissa axis denotes frequency f and each ordinate axis denotes signal intensity $S1(f)$, $S2(f)$ at frequency f. When the first MR data is acquired by the first sequence with applying a STIR pulse to generate the first frequency spectrum, one peak appears on the first frequency spectrum as shown in FIG. 6 (A) because of suppression of fat signals. Therefore, the one peak on the first frequency spectrum detected by the peak detection part 40C can be easily determined to be the resonance frequency of water.

When the peak detection part 40C detected a frequency corresponding to the one peak with sufficient accuracy, the detection accuracy determining part 40D determines the detection accuracy of the peak is sufficient as described above. The decision of whether the detection accuracy of the peak is sufficient or not can be performed by determining whether a frequency range, in which the signal intensity is not less than a threshold, is not more than another threshold or threshold determination of a statistical index such as a standard deviation.

However, when the detection accuracy determining part 40D determined that the accuracy was not sufficient, the second MR data is acquired by the second sequence without applying any STIR pulse for example though one peak was detected by the peak detection part 40C as shown by FIG. 6 (A). In this case, the second MR data is not influenced by fat suppression effect. Therefore, when the second frequency spectrum is generated from the second MR data, two peaks, respectively corresponding to the resonance frequencies of fat and water, appear on the second frequency spectrum as shown in FIG. 6 (B).

The resonance frequency of fat is distant from that of water by 3.5 ppm in the negative side. Therefore, the higher frequency of the frequencies corresponding to the two peaks indicates the resonance frequency of water and the lower one does that of fat. In the example shown in FIG. 6 (B), the peak in the higher frequency side shows the larger signal intensity. Therefore, at least detecting the respective maximum values of the first and second frequency spectra by the peak detection part 40C and relative positioning between the first and second frequency spectra so that the frequencies corresponding to the respective maximum values become mutually the same as determined by the subtraction calculating part 40E makes it possible to match the resonance frequencies of water on the first and second frequency spectra relatively as shown in FIG. 6 without detecting the second peak on the second frequency spectrum.

Hence, a difference Dp between peak values corresponding to fat signals can be calculated as a difference between signal intensities P1, P2 at a frequency lower than the frequency corresponding to the maximum values of the first and second frequency spectra by 3.5 ppm in the negative side as shown by equation (1).

$$Dp = P2 - P1 \quad (1)$$

Further, when a lower frequency f1 and a higher frequency f2, than the frequency lower than the frequency corresponding to the maximum values of the first and second frequency spectra by 3.5 ppm in the negative side, are set, a difference Di between integral values of the fat signals S1(f), S2(f) can be calculated as shown by equation (2).

$$Di = \int_{f1}^{f2} \{S2(f) - S1(f)\} df \quad (2)$$

Note that, when a frequency spectrum as shown in FIG. 6 is acquired at plural positions, an integral value of signals becomes a volume of a range surrounded by a curved surface representing a signal distribution having a positional direction axis. On the other hand, when a frequency spectrum is acquired at a single position, an integral value of signals becomes an area of a range surrounded by a curve representing a signal distribution. Therefore, it is preferable to perform a surface fitting or a curve fitting of the first and second frequency spectra as a preprocessing for calculating an integral value with higher accuracy.

Further, a difference of peak values and a difference of integral values corresponding to water signals can be also calculated similarly using a frequency corresponding to the maximum values of the first and second frequency spectra as a reference. However, intensities of water signals do not change according to fat suppression conditions including whether a STIR pulse is applied or not so much.

Therefore, when an integral range Δf is set to be large sufficiently so as to include the resonance frequencies of fat and water surely, the water signals are cancelled by subtraction. Consequently, a difference of integral values can be considered as a difference of integral values of fat signals. In this case, relative positioning processing of frequencies between the first and second frequency spectra is not necessary.

Figure 7:
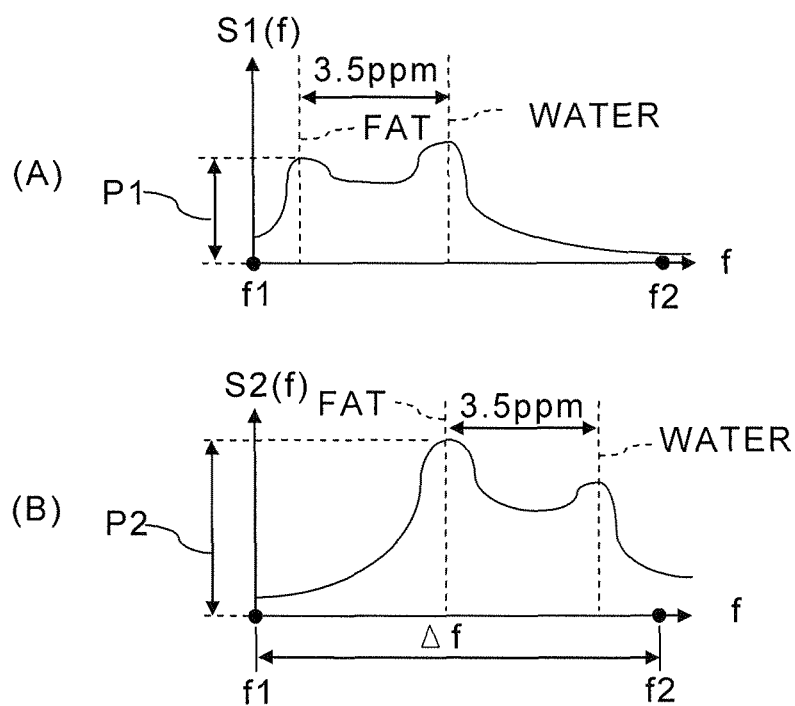
FIG. 7 shows the second example of two frequency spectra generated by the frequency spectrum generating part shown in FIG. 2.

FIG. 7 shows the second example of two frequency spectra generated by the frequency spectrum generating part 40B shown in FIG. 2.

In (A) and (B) of FIG. 7, each abscissa axis denotes frequency f and each ordinate axis denotes signal intensity S1(f), S2(f) at frequency f. When the first MR data is acquired from a part having much fat component such as a breast by the first sequence by applying a STIR pulse to generate the first frequency spectrum, fat signals are not sometimes suppressed sufficiently. In this case, two unclear peaks respectively corresponding to the resonance frequencies of fat and water appear at frequencies relatively distant by 3.5 ppm as shown in FIG. 7 (A).

Alternatively, when the second MR data is acquired from a part having fat component much by the second sequence without applying any STIR pulse to generate the second frequency spectrum, two peaks respectively corresponding to the resonance frequencies of fat and water sometimes appear as shown in FIG. 7 (B). In this case, signal intensity sometimes becomes the maximum at the resonance frequency of fat.

Further, when the first frequency spectrum shows the maximum signal intensity at the resonance frequency of water as shown in FIG. 7 (A), relative positioning of frequencies corresponding to the respective maximum values of the first and second frequency spectra inappropriately relates the resonance frequency of water on the first frequency spectrum with that of fat on the second frequency spectrum as shown in FIG. 7.

Accordingly, in such a case, it is necessary to detect two peaks on the first and second frequency spectra and relative positions between the peaks by the peak detection part 40C, and subsequently, perform relative shift correction processing in frequency by 3.5 ppm to the first and second frequency spectra as a preprocessing before calculating a difference Dp between peak values corresponding to fat signals by equation (1) in the subtraction calculating part 40E.

However, setting a large integral range Δf beyond twice the distance in resonance frequency between fat and water as shown in FIG. 7 makes it possible to calculate a difference between integral values of fat signals without relative shift correction processing of frequencies since intensities of water signals do not change remarkably according to conditions for fat suppression. Therefore, at least the respective maximum values of the first and second frequency spectra have only to be detected.

On the other hand, performing processing to correct a relative deviation of frequencies can calculate a difference between integral values of fat signals with higher accuracy by setting an integral range to be about a frequency range corresponding to a peak of the fat signals. In addition, a difference between integral values of water signals can also be calculated.

The resonance frequency detection part 40F has a function to determine which of the two frequency spectrum bases to detect the resonance frequency of water based on a calculation result of an index in the subtraction calculating part 40E and a function to obtain the resonance frequency of water based on the decided frequency spectrum, if necessary, by detecting the resonance frequency of fat. In addition, the resonance frequency detection part 40F is configured to detect the resonance frequency of water based on a peak detected from a firstly acquired frequency spectrum when whether the resonance frequency of water was detected with necessary accuracy or not is decided in the detection accuracy determining part 40D.

As shown in FIG. 6 (A), a frequency spectrum acquired from a part having a little fat component with fat suppression has a peak corresponding to water signals clearer than that corresponding to fat signals. Therefore, it is preferable to obtain the resonance frequency of water based on a peak corresponding to the water signals in view of improving accuracy.

However, a frequency spectrum acquired from a part having much fat component without fat suppression sometimes has a peak corresponding to fat signals clearer than that corresponding to water as shown in FIG. 7 (B). In this case, is considered that it is desired, in view of improving accuracy, to obtain the resonance frequency of fat based on a peak corresponding to fat signals to assume a frequency higher than the obtained resonance frequency of fat by 3.5 ppm as the resonance frequency of water.

When an amount of fat component is medium, it may be difficult to decide which of peaks corresponding to water signals and fat signals should be used to obtain the resonance frequency of water by observation of a user.

For that reason, the resonance frequency detection part 40F is configured to be able to determine which of peaks corresponding to water signals and fat signals is used to obtain the resonance frequency of water uniformly. This decision can be performed by threshold processing of an index.

For example, a part having much fat component shows insufficient fat suppression effect by applying a STIR pulse. However, intensities off at signals vary remarkably depending on whether a STIR pulse is applied or not due to the much fat component. On the contrary, in a part having a little fat component, fat signals are suppressed by applying a STIR pulse, and intensities of the fat signals vary a little due to whether a STIR pulse is applied or not, compared to a part having much fat component. In addition, when attention is given to intensities of water signals, a part having a little fat component shows a small variation in absolute intensities of water signals depending on whether a STIR pulse is applied or not.

Accordingly, when an index representing differences or ratios in intensities of fat signals or water signals between the first frequency spectrum acquired by applying a STIR pulse and the second frequency spectrum acquired without applying any STIR pulse is lower than a threshold, a part can be determined to have a little fat component. Then, calculation of the resonance frequency of water based on a peak of the first frequency spectrum acquired by applying a STIR pulse can be determined. On the contrary, the index representing the differences or the ratios in intensities of the fat signals between the first and the second frequency spectra is larger than the threshold, a part can be determined to have much fat component. Then, calculation of the resonance frequency of fat based on a peak corresponding to fat signals on the second frequency spectrum acquired without applying any STIR pulse can be determined. In this case, the resonance frequency of water is calculated based on the calculated resonance frequency of fat.

That is, the resonance frequency detection part 40F is configured to obtain the resonance frequency of fat using the frequency spectrum showing smaller fat suppression effect when an index representing differences in intensities of signals from fat is determined to be large by threshold processing to obtain the resonance frequency of water based on the obtained resonance frequency of fat. On the other hand, the resonance frequency detection part 40F is configured to obtain the resonance frequency of water using the frequency spectrum showing large fat suppression effect when an index is determined to be small by threshold processing. As an index to be a target of threshold processing, a difference or a ratio between integral values of curves representing intensities of signals from fat can be used. Alternatively, a difference or a ratio between peaks of intensities of signals from fat may be used as an index.

Note that, as a method for obtaining a resonance frequency from a peak on a frequency spectrum, not only a method in which a frequency corresponding to a local maximum value of signals is considered as a resonance frequency, but a method in which a frequency corresponding to the barycenter of a signal intensity distribution on a frequency spectrum is considered as a resonance frequency, a method in which a frequency corresponding to the center of a half bandwidth of signal intensity distribution on a frequency spectrum is considered as a resonance frequency or the like may be adopted.

The center frequency setting part 40G has a function to set a center frequency of RF pulses for imaging to the resonance frequency of water calculated by the resonance frequency detection part 40F.

The data processing unit 41 has a function to receive raw data from the sequence controller 31 to arrange in k-space formed in the k-space data storage unit 42, a function to receive MR data, for generating a frequency spectrum, from the sequence controller 31 to supply the MR data to the frequency spectrum generating part 40B, a function to acquire k-space data for imaging from the k-space data storage unit 42 to generate image data by necessary data processing including image reconstruction processing, a function to write the generated image data to the image data storage unit 43 and a function to read desired image data from the image data storage unit 43 to display the read image data on the display unit 34 with necessary image processing of the read image data.

So far, an example of fat suppression has been described. However, the resonance frequency of water can be obtained similarly also in case of suppressing fat signals relatively by water excitation. However, intensities of water signals vary remarkably depending on whether water excitation is performed. For that reason, an index representing a difference in intensity distribution of water signals between frequency spectra may be specified, and a frequency spectrum for obtaining the resonance frequency of water by threshold processing with regard to an index for water signals may be determined.

Further, a case of acquiring two frequency spectra has been described in the above mentioned example. However, three and above frequency spectra may be acquired. In this case, an index representing a difference in signal intensity distribution can be specified in a desired method. Consequently, a single one of plural frequency spectra used for calculating a resonance frequency can be determined based on the index.

Then, the operation and action of the magnetic resonance imaging apparatus 20 will be described.

Figure 8:
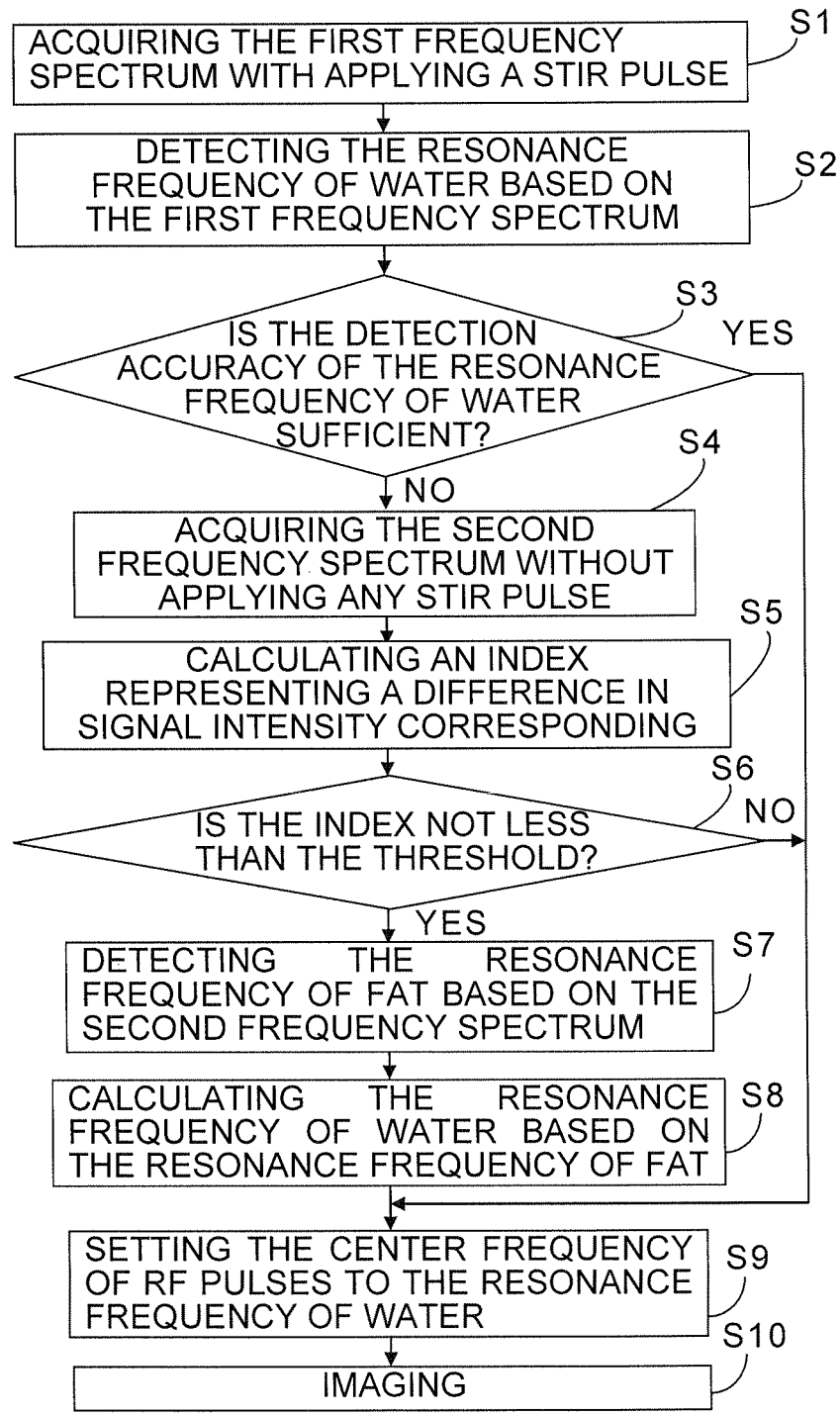
FIG. 8 is a flowchart showing an example of flow for imaging with adjusting the center frequency of RF pulses with the resonance frequency of water by the magnetic resonance imaging apparatus shown in FIG. 1.

FIG. 8 is a flowchart showing an example of flow for imaging with adjusting the center frequency of RF pulses with the resonance frequency of water by the magnetic resonance imaging apparatus 20 shown in FIG. 1. Here, an example case of acquiring the first and second frequency spectrum by the first sequence applying a STIR pulse and the second sequence without applying a STIR pulse in order to obtain the resonance frequency of water will be described.

Firstly, the object P is set to the bed 37 in advance, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

Then, in the step S1, the first frequency spectrum is acquired by the first sequence applying a STIR pulse. Specifically, the pulse sequence setting part 40A of the imaging condition setting unit 40 sets the first sequence for acquiring data after applying a STIR pulse as shown in FIG. 3 (A) as imaging conditions for a pre-scan. Then, the imaging conditions for the pre-scan including the first sequence are outputted from the imaging condition setting unit 40 to the sequence controller 31.

Next, the sequence controller 31 drives the gradient power supply 27, the transmitter 29, and the receiver 30 in accordance with the imaging conditions for the pre-scan, thereby generating a gradient magnetic field at the imaging area having the set object P, and further generating RF signals from the RF coil 24.

Consequently, the RF coil 24 receives MR signals generated due to nuclear magnetic resonance in the object P. Then, the receiver 30 receives the MR signals from the RF coil 24 and generates digital data of the MR signals. The receiver 30 supplies the generated data to the sequence controller 31. The sequence controller 31 supplies the MR signals to the data processing unit 41. The data processing unit 41 supplies the MR signals to the frequency spectrum generating part 40B.

Next, the frequency spectrum generating part 40B generates the first frequency spectrum based on the first MR data acquired by the first sequence.

Next, in the step S2, the peak detection part 40C detects the peak of the first frequency spectrum and the frequency corresponding to the peak. If one peak was detected, the resonance frequency detection part 40F recognizes a frequency corresponding to the detected peak as the resonance frequency of water. On the contrary, if two peaks were detected with the frequency distance of 3.5 ppm relatively, the resonance frequency detection part 40F recognizes a frequency corresponding to the peak in the higher frequency side as the resonance frequency of water.

Next, in the step S3, the detection accuracy determining part 40D determines whether the resonance frequency of water was detected with required accuracy or not. When the resonance frequency of water was not determined to be detected with required accuracy, the second frequency spectrum is acquired by the second sequence without applying a STIR pulse in the step S4

Specifically, the detection accuracy determining part 40D supplies instruction for generating the second sequence with the pulse sequence setting part 40A. Then, the pulse sequence setting part 40A sets the second sequence without applying a STIR pulse as imaging conditions for a pre-scan as shown in FIG. 3 (B). Further, the second frequency spectrum is acquired in s similar flow to that for acquiring the first frequency spectrum. In addition, peaks of the second frequency spectrum and frequencies corresponding to the peaks are detected by the peak detection part 40C.

Next, in the step S5, the subtraction calculating part 40E calculates an index representing a difference in intensities of fat signals between the first and second frequency spectrum. As the index, a difference Dp or a ratio between peak values P1, P2 corresponding to the fat signals as shown by equation (1), or a difference Di or a ratio between integral values of fat signals S1(f), S2(f) as shown by equation (2) can be used. In addition, when the second frequency spectrum shows the maximum value by fat signals as shown in FIG. 7 (B), a frequency distance between the first and second frequency spectrum is corrected, as needed.

Next, in the step S6, the resonance frequency detection part 40F performs threshold decision of the index representing a difference in intensities of fat signals. When it is determined that the index in not less than the threshold, it is considered that the peak corresponding to the fat signals becomes clearer than that corresponding to the water signals since an imaging part includes much fat component. Therefore, in the step S7, the resonance frequency detection part 40F obtains the resonance frequency of fat based on the peak corresponding to the fat signals Next, in the step S8, the resonance frequency detection part 40F calculates a frequency higher than the resonance frequency of fat by 3.5 ppm as the resonance frequency of water. Consequently, the resonance frequency of water is obtained.

When the detection accuracy determining part 40D determined that the resonance frequency of water was detected with the required accuracy in the determination of the step S3, the detection accuracy determining part 40D gives instruction to the pulse sequence setting part 40A so as not to generate the second sequence. Therefore, the second frequency spectrum is not acquired. In this case, a frequency corresponding to the peak detected by the peak detection part 40C in the step S2 is recognized as the resonance frequency of water.

Alternatively, the resonance frequency detection part 40F determined that the index representing the difference in the intensities of the fat signals was less than the threshold in the determination in the step S6, it is considered that the peak corresponding to the water signals becomes clearer than that corresponding to the fat signals since the imaging part has a little fat component. Also in this case, the frequency corresponding to the peak detected by the peak detection part 40C in the step S2 is recognized as the resonance frequency of water.

Next, in the step S9, the center frequency setting part 40G sets the center frequency of RF pulses for imaging to the resonance frequency of water. In addition, the other imaging conditions including a pulse sequence for imaging are set by the imaging condition setting unit 40.

Next in the step S10, imaging is performed using the RF pulses of which center frequency was set to the resonance frequency of water as an example of the specific material or another one. Specifically, the imaging condition setting unit 40 outputs the imaging conditions for imaging to the sequence controller 31. Consequently, MR data for imaging is acquired in a similar flow to that for a pre-scan. The acquired MR data is arranged in k-space formed in the k-space data storage unit 42 by the data processing unit 41.

Next, the data processing unit 41 performs image reconstruction processing of the MR data and image processing to generate image data for displaying. The generated image data is displayed on the display unit 34. In addition, necessary image data is stored in the image data storage unit 43.

As mentioned above, the magnetic resonance imaging apparatus 20 is an apparatus configured to acquire plural frequency spectra with regard to MR signals under mutually different conditions influencing suppression or enhancing effect for a specific material such as fat to detect a resonance frequency of the specific material or another material for setting the center frequency of RF pulses using a frequency spectrum selected according to an index representing a difference in signal intensities from the specific material between the frequency spectra. In a case of obtaining the resonance frequency of water signals, a frequency spectrum showing large suppression effect of fat signals and a frequency spectrum showing small suppression effect of the fat signals are acquired, for example. When a difference in intensities of the fat signals is large, the resonance frequency of the fat signals is detected from the frequency spectrum showing small suppression effect of the fat signals. Subsequently, the resonance frequency of water is calculated from the resonance frequency of the fat signals based on the chemical shift amount between the fat signals and the water signals. On the contrary, when the difference in intensities of the fat signals is small, the resonance frequency of the water signals is detected from the frequency spectrum showing large suppression effect of the fat signals.

Therefore, in case of obtaining the resonance frequency of water, the magnetic resonance imaging apparatus 20 makes it possible to obtain the resonance frequency of water with higher accuracy even though an imaging part includes much fat component and fat suppression effect is insufficient. Hence, the magnetic resonance imaging apparatus 20 is effective for imaging a breast part having much fat component. Further, a resonance frequency of another material can be also detected with high accuracy.

Consequently, a center frequency of RF pulses can be set into a more appropriate value. Especially, in case of acquiring an image of which fat component is suppressed with use of chemical shift, an image can be acquired with suppressing fat signals satisfactorily.

In addition, the magnetic resonance imaging apparatus 20 can improve determination accuracy of whether a peak detected on a frequency spectrum corresponds to the resonance frequency of water or the resonance frequency of fat to automatically detect a resonance frequency and set a center frequency of RF pulses easily.

Second Embodiment

The magnetic resonance imaging apparatus in the second embodiment has the resonance frequency detection part 40F of which functions differently from that in the first embodiment. The other configurations and functions of the magnetic resonance imaging apparatus in the second embodiment are similar to those in the first embodiment. Accordingly, the same signs are attached and their explanations are omitted. Mainly, functions of the resonance frequency detection part 40F will be described.

Specifically, the resonance frequency detection part 40F of the magnetic resonance imaging apparatus in the second embodiment has a function to obtain the resonance frequency of water in another way. That is, signal rates, between plural frequency spectra showing mutually different fat suppression effects, in frequency bands corresponding to the respective maximum values of the plural frequency spectra are obtained. Subsequently, ratios of the signal rates between the first plural frequency bands and the second plural frequency bands different from the first plural frequency bands by predetermined frequencies respectively are obtained. Then, the resonance frequency of water is obtained based on the signal rates and the ratios of the signal rates.

In other words, the resonance frequency detection part 40F is configured to use a rate of change in signal amount as each index representing a difference in intensities of MR signals from water or fat between plural frequency spectra. Further, the resonance frequency detection part 40F is configured to obtain the resonance frequency of water based on signal rates between plural frequency spectra and other signal rates between frequency bands relatively distant by a predetermined frequency, e.g., 3.5 ppm.

In addition, a function to perform noise determination processing is provided with the resonance frequency detection part 40F, as needed. The noise determination processing is processing which performs determination of whether a signal amount consisting of noise component was used for calculating a rate of signal amounts based on a deviation of signal amounts between frequency spectra showing mutually different fat suppression effects. The deviation is obtained in a frequency band lower than that corresponding to the respective maximum values on the frequency spectra by 3.5 ppm. The noise determination processing also includes processing to correct a rate of signal amounts into a constant value when it was determined that a signal amount consisting of noise component had been used Hereinafter, description will be made with referring to an example of obtaining the resonance frequency of water based on the first frequency spectrum acquired with applying a STIR pulse as an example of a fat saturation pulse and the second frequency spectrum acquired without applying a STIR pulse. Same applies to a case of changing a FA of a fat saturation pulse as shown in FIG. 4 and a case of changing an elapse time from an application time of a fat saturation pulse as shown in FIG. 5.

Figure 9:
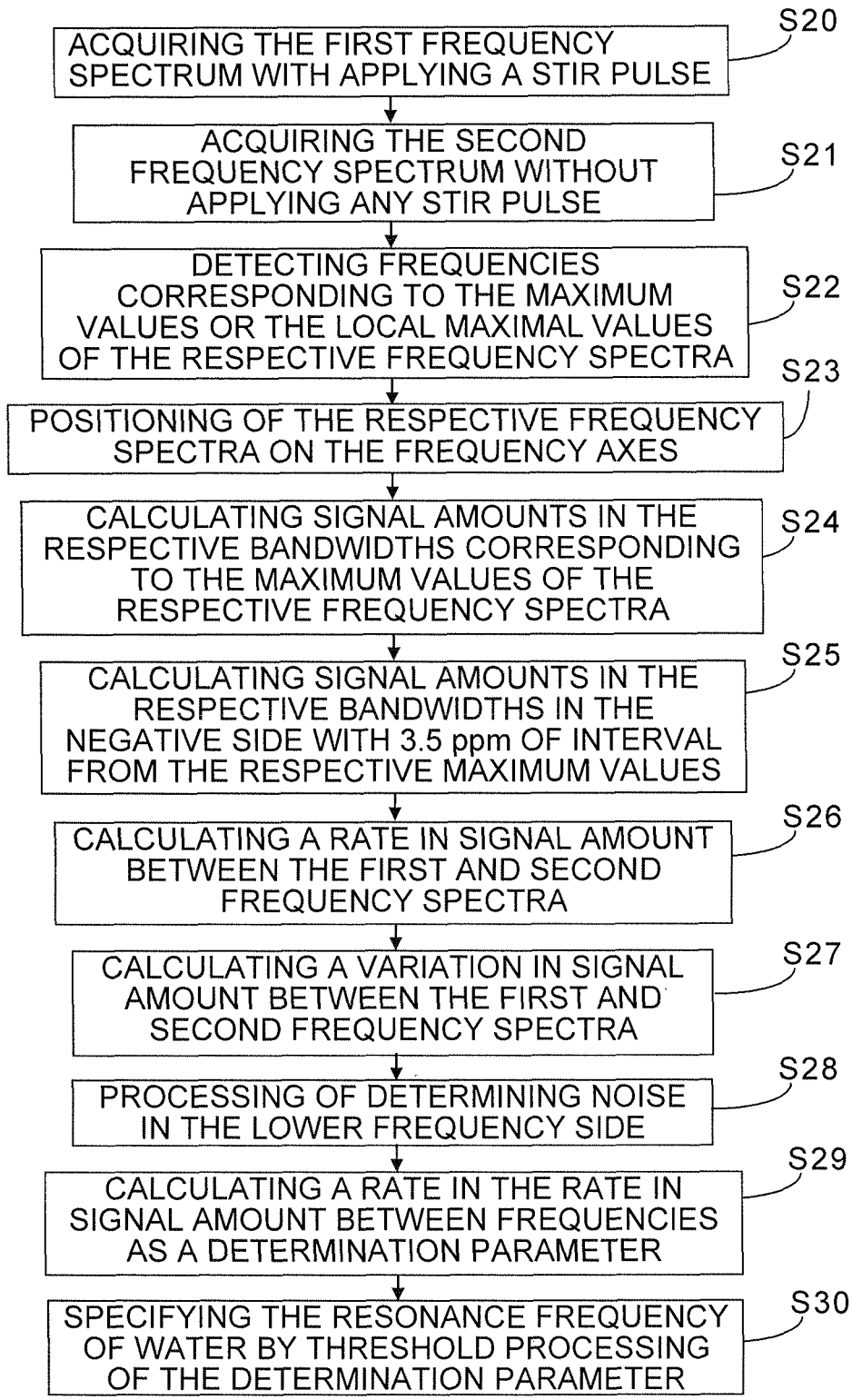
FIG. 9 is a flowchart showing a flow of processing to detect the resonance frequency of water performed by the magnetic resonance imaging apparatus according to the second embodiment of the present invention.

FIG. 9 is a flowchart showing a flow of processing to detect the resonance frequency of water performed by the magnetic resonance imaging apparatus according to the second embodiment of the present invention.

Firstly, in the step S20, the first frequency spectrum is acquired with applying a STIR pulse. Specifically, MR signals for generating the first frequency spectrum are acquired by a pre-scan with applying a STIR pulse similarly to the step S shown in FIG. 8. Subsequently, the first frequency spectrum is generated in the frequency spectrum generating part 40B.

Next, in the step S21, the second frequency spectrum is acquired without applying a STIR pulse. Specifically, MR signals for generating the second frequency spectrum are acquired by a pre-scan without applying a STIR pulse similarly to the step S4 shown in FIG. 8. Subsequently, the second frequency spectrum is generated in the frequency spectrum generating part 40B.

Note that, determination of whether detection accuracy of the resonance frequency of water is sufficient or not may be performed similarly to FIG. 8. Therefore, the second frequency spectrum may not be acquired when it was determined that detection accuracy of the resonance frequency of water was sufficient.

Next, in the step S22, the peak detection part 40C detects frequencies $f0_{STIR}$, $f0$ corresponding to the maximum values on the first and second frequency spectra. Alternatively, the peak detection part 40C detects frequencies $f0'_{STIR}$, $f0'$ corresponding to local maximum values when the local maximum values are detected as second peaks in the negative side of the maximum values on the first and second frequency spectra by 3.5 ppm respectively.

Which of the frequency $f0_{STIR}$, $f0$ corresponding to the maximum values or the frequency $f0'_{STIR}$, $f0'$ corresponding to the local maximum values is adopted to subsequent processing can be determined according to an arbitrary algorithm. For example, the following algorithm can be made. If a local maximum value not more than 1/Y (Y is a positive value more than 1) of the maximum value was detected at the frequency $f0'_{STIR}$, $f0'$ in the negative side of the frequency $f0_{STIR}$, $f0$ corresponding to the maximum values by 3.5 ppm, the frequency $f0_{STIR}$, $f0$ corresponding to the maximum values can be assumed to be the resonance frequency of water so as to be adopted in the subsequent processing. On the contrary, a local maximum value more than 1/Y of the maximum value was detected at the frequency $f0'_{STIR}$, $f0'$ in the negative side of the frequency $f0_{STIR}$, $f0$ corresponding to the maximum values by 3.5 ppm, the frequency $f0'_{STIR}$, $f0'$ corresponding to the local maximum value can be assumed to be the resonance frequency of fat so as to be adopted in the subsequent processing.

Next, in the step S23, the resonance frequency detection part 40F matches positions of the first and second frequency spectra on the frequency axis.

Figure 10:
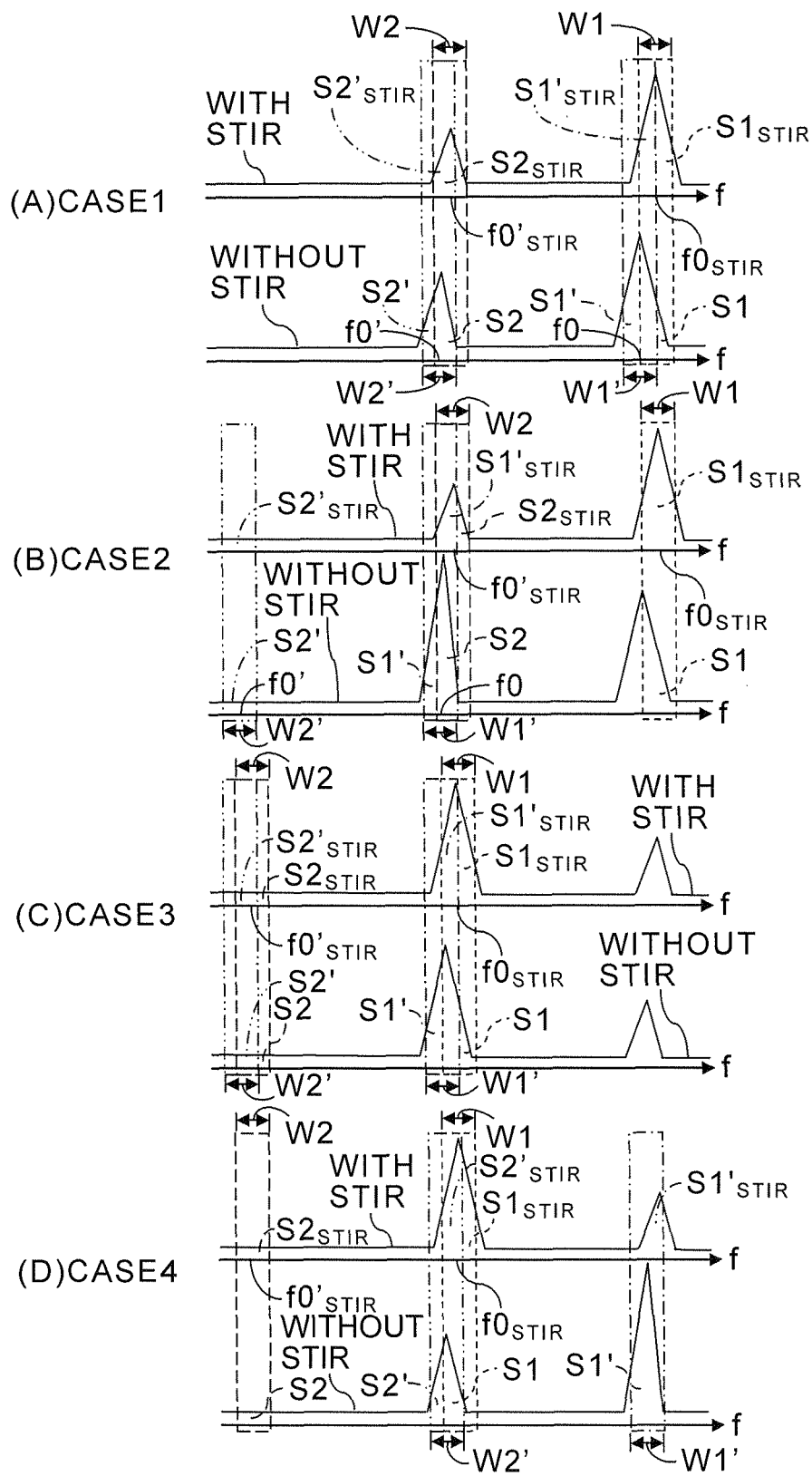
FIG. 10 is a diagram showing combinations of the first frequency spectrum and the second frequency spectrum possibly acquired in step S20 and step S21 shown in FIG. 9.

FIG. 10 is a diagram showing combinations of the first frequency spectrum and the second frequency spectrum possibly acquired in step S20 and step S21 shown in FIG. 9.

The respective upper sides of FIGS. 10 (A), (B), (C) and (D) shows examples of the first frequency spectra acquired with applying a STIR pulse. On the other hand, the respective lower sides of FIGS. 10 (A), (B), (C) and (D) shows examples of the second frequency spectra acquired without applying a STIR pulse. Therefore, each abscissa axis in FIG. 10 denotes frequency f. FIGS. 10 (A), (B), (C) and (D)

respectively show the possible cases (CASE1, CASE2, CASE3, CASE4) as combinations of the first and second frequency spectra.

When a frequency spectrum is acquired from an imaging part having relatively little fat such as head part without applying a STIR pulse, the second frequency spectrum showing the maximum value at the resonance frequency of water and a local maximum value lower than the maximum value at the resonance frequency of fat is obtained. In this case, by acquiring a frequency spectrum after applying a STIR pulse, the first frequency spectrum showing an intensity lower than that of the second frequency spectrum at the resonance frequency of fat is obtained. Therefore, a relationship between the first frequency spectrum and the second frequency spectrum becomes the CASE1 as shown in FIG. 10.(A).

When frequencies $f0_{STIR}$, $f0$ corresponding to the respective maximum values of the first frequency spectrum and the second frequency spectrum as shown in FIG. 10 (A) are detected respectively, both the frequencies $f0_{STIR}$, $f0$ corresponding to the respective maximum values become the resonance frequency of water.

On the other hand, when a frequency spectrum is acquired from an imaging part having fat without a STIR pulse, the second frequency spectrum showing the maximum value at the resonance frequency of fat and a local maximum value lower than the maximum value at the resonance frequency of water is obtained in many cases. In this case, when a frequency spectrum is acquired in a state in which fat suppression effect is obtained sufficiently by applying a STIR pulse, the first frequency spectrum showing the maximum value at the resonance frequency of water and a local maximum value lower than the maximum value at the resonance frequency of fat is obtained. Therefore, a relationship between the first frequency spectrum and the second frequency spectrum become the CASE2 as shown in FIG. 10 (B).

When the frequencies $f0_{STIR}$, $f0$ corresponding to the respective maximum value of the first frequency spectrum and the second frequency spectrum as shown in FIG. 10 (B) are respectively detected, the frequency $f0_{STIR}$ corresponding to the maximum value of the first frequency spectrum becomes the resonance frequency of water but the frequency $f0$ corresponding to the maximum value of the second frequency spectrum becomes the resonance frequency of fat. The CASE2 shown in FIG. 10 (B) is the typical case.

When a frequency spectrum is acquired from an imaging part having relatively much fat without applying a STIR pulse, the second frequency spectrum showing the maximum value at the resonance frequency of fat and a local maximum value lower than the maximum value at the resonance frequency of water is obtained. In this case, sufficient fat suppression effect cannot be obtained in spite of applying a STIR pulse. Accordingly, the first frequency spectrum showing the maximum value at the resonance frequency of fat and a local maximum value lower than the maximum value at the resonance frequency of water is obtained. Therefore, a relationship between the first frequency spectrum and the second frequency spectrum becomes the CASE3 as shown in FIG. 10 (C).

When the frequencies $f0_{STIR}$, $f0$ corresponding to the respective maximum values of the first frequency spectrum and the second frequency spectrum as shown in FIG. 10 (C) are detected, both the frequencies $f0_{STIR}$, $f0$ corresponding to the maximum values and assumed to be the resonance frequency of water actually become the resonance frequencies of fat.

In addition, the case shown in FIG. 10 (D) is possible as the rare CASE4. In the CASE4, a frequency $f_{STIR}$ corresponding to the maximum value of the first frequency spectrum acquired with applying a STIR pulse indicates the resonance frequency of fat while a frequency $f0$ corresponding to the maximum value of the second frequency spectrum acquired without applying a STIR pulse indicates the resonance frequency of water.

Next, in the step S24, the resonance frequency detection part 40F calculates a signal amount $S1_{STIR}$ in a bandwidth W1 [Hz] including the frequency $f0_{STIR}$ corresponding to the maximum value of the first frequency spectrum acquired after applying a STIR pulse. Meanwhile, the resonance frequency detection part 40F calculates a signal amount S1 in the bandwidth W1 of the second frequency spectrum acquired without applying a STIR pulse.

Further, a signal amount S1' of the second frequency spectrum in a bandwidth W1' including the frequency $f0$ corresponding to the maximum value of the second frequency spectrum acquired without applying a STIR pulse is calculated by the resonance frequency detection part 40F. Meanwhile, a signal amount $S1'_{STIR}$ in the bandwidth W1' of the first frequency spectrum acquired after applying a STIR pulse is calculated by the resonance frequency detection part 40F.

The respective signal amounts $S1_{STIR}$, S1, $S1'_{STIR}$, and S1' can be calculated by integral processing as areas of parts surrounded by the frequency axis and the curves indicating the first and second frequency spectra respectively as shown in FIG. 10. In this case, the bandwidths W1, W1' can be set to half widths of the first and second frequency spectra and the like. Alternatively, signal intensities at the maximum values or the centers of half widths of the first and second frequency spectra may be used as the respective signal amounts $S1_{STIR}$, S1, $S1'_{STIR}$, S1'. In this case, the bandwidths W1, W1' become a unit width. However, it is preferable for accuracy to use areas as the respective signal amounts $S1_{STIR}$, S1, $S1'_{STIR}$, S1'. Accordingly, an example case of obtaining the respective signal amounts $S1_{STIR}$, S1, $S1'_{STIR}$, S1' as areas will be described hereinafter.

Next, in the step S25, the resonance frequency detection part 40F calculates a signal amount $S2_{STIR}$ in a bandwidth W2 including a frequency in the negative side of the frequency $f0_{STIR}$ corresponding to the maximum value of the first frequency spectrum by 3.5 ppm. Meanwhile, the resonance frequency detection part 40F calculates a signal amount S2 in the bandwidth W2 of the second frequency spectrum acquired without applying a STIR pulse.

Further, a signal amount S2' of the second frequency spectrum, acquired without applying a STIR pulse, in a bandwidth W2' including a frequency in the negative side of the frequency $f0$ corresponding to the maximum value of the second frequency spectrum by 3.5 ppm is calculated by the resonance frequency detection part 40F. Meanwhile, a signal amount $S2'_{STIR}$ of the first frequency spectrum, acquired with applying a STIR pulse, in the bandwidth W2' is calculated by the resonance frequency detection part 40F.

Note that, the respective signal amounts $S2_{STIR}$, S2, $S2'_{STIR}$, S2' can be calculated similarly to the respective signal amounts $S1_{STIR}$, S1, $S1'_{STIR}$, S1' in the positive side by 3.5 ppm. The bandwidth W2, W2' can be also determined similarly to the bandwidth W1, W1' in the positive side by 3.5 ppm.

Moreover, when frequencies $f0'_{STIR}$, $f0'$ corresponding to the second local maximum values of the first and second frequency spectra were detected instead of the frequency $f0_{STIR}$, $f0$ corresponding to the maximum values of the first and second frequency spectra, the respective signal amounts $S2_{STIR}$, S2, $S2'_{STIR}$, S2' in the lower frequency side on the basis of the frequencies $f0'_{STIR}$, f0' corresponding to the second local maximum values are calculated. Meanwhile, the respective signal amounts $S1_{STIR}$, S1, $S1'_{STIR}$, S1' in the higher frequency side on the basis of the frequency in the positive side of the frequencies $f0'_{STIR}$, f0' corresponding to the local maximum values by 3.5 ppm are calculated.

Next, in the step S26, the resonance frequency detection part 40F calculates respective rates R1, R2, R1', R2' of the signal amounts between the first and the second frequency spectrum in the respective bandwidths W1, W1',W2, W2'. The respective rates R1, R2, R1', R2' can be calculated by equations (3-1), (3-2), (3-3) and (3-4) respectively.

$$R1=S1/S1_{STIR} \quad (3-1)$$

$$R2=S2/S2_{STIR} \quad (3-2)$$

$$R1'=S1'/S1'_{STIR} \quad (3-3)$$

$$R2'=S2'/S2'_{STIR} \quad (3-4)$$

Next, in the step S27, the resonance frequency detection part 40F calculates variations A, B of the respective signal amounts $S2_{STIR}$, S2, $S2'_{STIR}$, S2' in the lower frequency side between the first and second frequency spectra. The variations A, B of the respective signal amounts $S2_{STIR}$, S2, $S2'_{STIR}$, S2' can be calculated as subtraction values between the areas by equations (4-1) and (4-2) respectively.

$$A=S2_{STIR}-S2 \quad (4-1)$$

$$B=S2_{STIR}-S2' \quad (4-2)$$

Next, in the step S28, the resonance frequency detection part 40F performs noise determination processing. In the noise determination processing, whether the respective signal amounts $S2_{STIR}$, S2, $S2'_{STIR}$, S2' having been used for calculation of the rates R2, R2' of the signal amounts in the lower frequency side were signal amounts of noise components is determined. Then, if it was determined that signal amounts of noise components had been used, the rates R2, R2' of the signal amounts are set to constant values. This noise determination processing can be performed in accordance with noise determination algorithm based on the variation A, B of the respective signal amounts $S2_{STIR}$, S2, $S2'_{STIR}$, S2' in the lower frequency side.

The noise determination algorithm is a processing for mandatorily allocating a constant value C to a rate R2, R2' of a signal amount determined to have been calculated using a signal amount of noise component. This noise determination algorithm can be defined as equation (5) for example.

$$R2=C1:|A/B|<TH1$$

$$R2'=C1:TH2<|A/B|$$

$$R2=R2'=C1:TH1\le|A/B|\le TH2,|B/\max(S1_{STIR},S1')|<TH3 \quad (5)$$

In equation (5), max( ) is function outputting the maximum value out of plural values. Further, TH1, TH2, TH3 are the first, second, third and fourth thresholds which can be set to be appropriate values through experiments, simulations or the like respectively. Similarly, the constant value C1 can be also set to an appropriate value through experiments, simulations or the like.

When a ratio of the variation A of the signals obtained by equation (4-1) to the variation B of the signals obtained by equation (4-2) is lower than the first threshold TH1, it is determined that the variation A of the signals obtained by equation (4-1) shows a slight variation between noise components. Therefore, the constant value C1 is substituted for the rate R2 obtained by equation (3-2) as shown by equation (5).

On the contrary, the ratio of the variation A of the signals obtained by equation (4-1) to the variation B of the signals obtained by equation (4-2) is larger than the second threshold TH2, it is determined that the variation B of the signals obtained by equation (4-2) shows a slight variation between noise components. Therefore, the constant value C1 is substituted for the rate R2' obtained by equation (3-4) as shown by equation (5).

Moreover, the ratio of the variation A of the signals obtained by equation (4-1) to the variation B of the signals obtained by equation (4-2) is not lower than the first threshold TH1 and not larger than the second threshold TH2 and a ratio of variation B of the signals in the lower frequency side to the larger one out of the signal amounts $S1_{STIR}$, S1' corresponding to the respective maximum values of the first and second frequency spectra is lower than the threshold TH3, it is determined that both the variations A, B of the signals in the lower frequency side become slight variations. Therefore, the constant value C1 is respectively substituted for both the rates R2, R2' obtained by equations (3-2) and (3-4) as shown by equation (5).

Note that, when it has been determined that a signal amount of noise component had not been used for calculation of the rates R2, R2' of the signal amounts in the lower frequency side in the threshold determination processing shown by equation (5), the rates R2, R2' of the signal amounts obtained as the calculation results by equations (3-2) and (3-4) are used for the subsequent processing as they are without substituting the constant value C1 for the rates R2, R2'.

Next, in the step S29, the resonance frequency detection part 40F calculates ratios of the respective rates R2, R2' of the signal amounts in the lower frequency side to the respective rates R1, R1' of the signal amounts in the higher frequency side as determination parameters T, T'. Specifically, the resonance frequency detection part 40F calculates the determination parameter T, T' as rates, of the rates R1, R2, R1', R2' of the signal amounts between the frequency spectra, between frequencies mutually distant by 3.5 ppm as shown by equations (6-1) and (6-2) respectively.

$$T=R2/R1 \quad (6-1)$$

$$T=R2'/R1' \quad (6-2)$$

Next, in the step S30, the resonance frequency detection part 40F specifies the resonance frequencies of water and fat by threshold processing to compare each of the determination parameter T, T' with a threshold ϵ. Specifying the resonance frequency of water can be performed in accordance with an algorithm for specifying the resonance frequency as mentioned below for example. Note that, the threshold a can be determined as a constant value in advance experimentally or by a simulation.

Firstly, when a result of the threshold determination is T>ϵ and T'>ϵ, the first and second frequency spectra can be determined to fall under the CASE1 shown in FIG. 10 (A). Therefore, the frequency $f0_{STIR}$ corresponding to the maximum value of the first frequency spectrum acquired with applying a STIR pulse can be specified as the resonance frequency of water.

Next, when the result of the threshold determination is T>ϵ and T'<ϵ, the first and second frequency spectra can be determined to fall under the CASE2 shown in FIG. 10 (B).

Therefore, also in this case, the frequency $f0_{STIR}$ corresponding to the maximum value of the first frequency spectrum acquired with applying a STIR pulse can be specified as the resonance frequency of water.

That is, when $T > \epsilon$, the frequency $f0_{STIR}$ corresponding to the maximum value of the first frequency spectrum acquired with applying a STIR pulse can be specified as the resonance frequency of water without the threshold determination of T'.

On the other hand, when the result of the threshold determination is $T < \epsilon$ and $T' < \epsilon$, a further threshold determination shown by equation (7) is performed.

$$R1 = S1/S1_{STIR} > X \qquad (7)$$

Note that, X in equation (7) is a threshold which can be determined experimentally or by a simulation in advance. The X is assumed to be a value more than 3 experimentally.

When equation (7) is true, the first and second frequency spectra can be determined to fall under the CASE3 shown in FIG. 10 (C). That is, it is determined that the resonance frequency of fat has been detected as the maximum values of the first and second frequency spectra. Therefore, in this case, the frequency higher than the frequency f0 corresponding to the maximum value of the second frequency spectrum acquired without applying a STIR pulse by 3.5 ppm can be specified as the resonance frequency of water.

On the contrary, equation (7) is not satisfied, the first and second frequency spectra can be determined to fall under the CASE1 shown in FIG. 10 (A). Therefore, the frequency $f0_{STIR}$ corresponding to the maximum value of the first frequency spectrum acquired with applying a STIR pulse can be specified as the resonance frequency of water.

On the other hand, when the result of the threshold determination is $T < \epsilon$ and $T' > \epsilon$, the first and second frequency spectra can be determined to fall under the CASE4 shown in FIG. 10 (D). Note that, the CASE4 is the rare case in which the first frequency spectrum acquired with applying a STIR pulse shows the maximum value at the resonance frequency of fat while the second frequency spectrum acquired without applying a STIR pulse shows the maximum value at the resonance frequency of water. In this case, the frequency $f0_{STIR}$ corresponding to the maximum value of the first frequency spectrum acquired with applying a STIR pulse indicates the resonance frequency of fat. Therefore, the frequency higher than the frequency $f0_{STIR}$ by 3.5 ppm can be specified as the resonance frequency of water.

By the magnetic resonance imaging apparatus in the second embodiment as described above, it is possible to determine whether a peak of a frequency spectrum corresponds to the resonance frequency of water or fat with high accuracy in various cases including a case in which an imaging part has little fat, a case in which MR signals are not acquired from water as such or the like. That is, the resonance frequencies of fat and water can be detected based on frequency spectra with high accuracy. As a result, the center frequency of RF pulses for imaging can be set appropriately to acquire MR images showing satisfactory fat suppression effect.

Especially, infinite approximation of determination parameters T, T', used for specifying the resonance frequency of water, to zero can be avoided by noise determination processing. Hence, it is possible to make the determination parameters T, T' using signals rates be stable values. In addition, processing for specifying the resonance frequency of water based on the determination parameters T, T' also can be performed stably with avoiding errors.

Third Embodiment

The magnetic resonance imaging apparatus in the third embodiment includes a resonance frequency detection part having functions different from those of the magnetic resonance imaging apparatus in each of the first and second embodiments. The other configurations and functions of the magnetic resonance imaging apparatus in the third embodiment are similar to those in each of the first and second embodiments. Accordingly, their explanations are omitted and only functions of the resonance frequency detection part will be described.

In the above mentioned first and second embodiments, a method for obtaining a resonance frequency of a specific material such as water and fat based on actually acquired frequency spectra has been explained. However, a resonance frequency of a specific material also can be obtained based on an actually acquired frequency spectrum and a frequency spectrum for reference of which shape was previously modeled according to each degree of suppression effect or enhancing effect of signals from the specific material.

To be more precise, a frequency spectrum of MR signals is acquired from an object while suppressing or enhancing signals from a specific material. Then, a resonance frequency of the specific material or another material can be obtained based on an index representing an equality degree or an inequality degree between the actually acquired frequency spectrum and a frequency spectrum for reference. In other words, a resonance frequency of a specific material such as water and fat can be obtained with a stochastic method by curve fitting.

As a method for fitting, a method for shifting a frequency spectrum so that a correlation coefficient as an index of equality degree becomes closer to 1, a method for shifting a frequency spectrum by a least squares method which minimizes a square error as an index of inequality degree and the like. That is, automatic determination that respective peaks detected from an actually acquired frequency spectrum correspond to resonance frequencies of which materials can be performed by shifting the actually acquired frequency spectrum in the frequency direction so that the equality degree between the actually acquired frequency spectrum and a frequency spectrum for reference become maximum.

For that purpose, when the magnetic resonance imaging apparatus has the configuration shown in FIG. 2, the resonance frequency detection part 40D has only to be provided with the automatic determination function of a resonance frequency based on an equality degree or an inequality degree between an actually acquired frequency spectrum and a frequency spectrum for reference as described above.

Other Embodiment

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance (MR) imaging apparatus comprising:
   MRI system components including static and gradient magnetic field generators, at least one radio frequency (RF) coil, an RF transmitter, an RF receiver and at least one computer configured to control said components to
   acquire frequency spectra including a first frequency spectrum of first MR signals and a second frequency spectrum of second MR signals from an object, said spectra exhibiting a changing suppression effect or a changing enhancing effect of signals from a specific material;
   obtain a resonance frequency of the specific material or another material using a frequency spectrum, for obtaining the resonance frequency of the specific material or the another material, selected from the first frequency spectrum and the second frequency spectrum based on an index representing a difference in intensities of signals from the specific material or the another material between the first frequency spectrum and the second frequency spectrum; and
   perform MR imaging using a radio frequency pulse having a center frequency set to the resonance frequency of the specific material or the another material.

2. The magnetic resonance imaging apparatus of claim 1, wherein
   the first and second frequency spectrums having fat suppression effects that are mutually different are acquired by (a) changing a flip angle of a fat saturation pulse or (b) applying or not applying a fat saturation pulse, and
   a resonance frequency of water is obtained using a frequency spectrum showing a larger fat suppression effect in a case where an index representing a difference in intensity of signals from fat is determined to be small by threshold processing and a resonance frequency of the fat is obtained using a frequency spectrum showing a smaller fat suppression effect in a case where the index is determined to be large by the threshold processing to obtain the resonance frequency of the water based on the obtained resonance frequency of the fat.

3. The magnetic resonance imaging apparatus of claim 2, wherein
   a difference or a rate between integral values of curves representing intensities of signals from the fat is used as the index.

4. The magnetic resonance imaging apparatus of claim 2, wherein
   a difference or a rate between peaks of intensities of signals from the fat is used as the index.

5. The magnetic resonance imaging apparatus of claim 2, wherein said at least one computer is further configured
   to determine whether the resonance frequency of the water was obtained with a predetermined accuracy using the frequency spectrum showing the larger fat suppression effect so as not to acquire the frequency spectrum showing the smaller fat suppression effect in a case where it was determined that the resonance frequency of the water had been obtained with the predetermined accuracy.

6. The magnetic resonance imaging apparatus of claim 1, wherein
   the first and second frequency spectrums showing mutually different degrees in suppression or enhancing effect of signals from the specific material are acquired based on a difference in longitudinal relaxation time between the specific material and the another material.

7. The magnetic resonance imaging apparatus of claim 1, wherein,
   a resonance frequency of water is obtained based on signal rates in first frequency bands between frequency spectra showing mutually different fat suppression effects and a ratio of the signal rates between the first frequency bands and second frequency bands respectively distant from the first frequency bands by a predetermined frequency, the frequency bands corresponding to respective maximum values of the frequency spectra.

8. A magnetic resonance (MR) imaging apparatus comprising:
   MRI system components including static and gradient magnetic field generators, at least one radio frequency (RF) coil, an RF transmitter, an RF receiver and at least one computer configured to control said components to
   acquire a frequency spectrum of magnetic resonance signals from an object with suppressing or enhancing signals from a specific material;
   obtain a resonance frequency of the specific material or another material by shifting the acquired frequency spectrum in a frequency direction based on an index representing an equality degree or an inequality degree between the frequency spectrum and a reference frequency spectrum; and
   perform MR imaging using a radio frequency pulse having a center frequency set to the resonance frequency of the specific material or the another material.

9. A magnetic resonance (MR) imaging method comprising:
   using MRI system components including static and gradient magnetic field generators, at least one radio frequency (RF) coil, an RF transmitter, an RF receiver and at least one computer configured to control said components to effect
   acquiring a first frequency spectrum of first MR signals and a second frequency spectrum of MR signals from an object, said spectra exhibiting a changing suppression effect or a changing enhancing effect of signals from a specific material;
   obtaining a resonance frequency of the specific material or another material using a frequency spectrum, for obtaining the resonance frequency of the specific material or the another material, selected from the first frequency spectrum and the second frequency spectrum based on an index representing a difference in intensities of signals from the specific material or the another material between the first and second frequency spectrums; and
   performing MR imaging using a radio frequency pulse having a center frequency set to the resonance frequency of the specific material or the another material.

* * * * *